United States Patent [19]

Golding et al.

[11] Patent Number: 5,023,386

[45] Date of Patent: Jun. 11, 1991

[54] PRODUCTION OF HEXANITROSTILBENE (HNS)

[75] Inventors: Peter Golding, Kings Langley; Asoka M. Jayaweera-Bandara, Long Ditton; Henry Duffin, Surbiton, all of England

[73] Assignee: Secretary of State for Defence in her Britannic Majesty's Government, London, United Kingdom

[21] Appl. No.: 457,681

[22] PCT Filed: May 26, 1988

[86] PCT No.: PCT/GB88/00420

§ 371 Date: Jan. 4, 1990

§ 102(e) Date: Jan. 4, 1990

[87] PCT Pub. No.: WO88/09784

PCT Pub. Date: Dec. 15, 1988

[30] Foreign Application Priority Data

Jun. 1, 1987 [GB] United Kingdom ............... 8712834

[51] Int. Cl.$^5$ ............................................ C07C 205/06
[52] U.S. Cl. ..................................... 568/931; 568/928
[58] Field of Search ................................. 568/931, 928

[56] References Cited

U.S. PATENT DOCUMENTS

| | | | |
|---|---|---|---|
| 3,505,413 | 4/1970 | Shipp | 568/931 |
| 4,243,614 | 1/1981 | Gilbert | 568/931 |
| 4,270,012 | 5/1981 | Gilbert | 568/931 |
| 4,626,606 | 12/1986 | Duffin et al. | 568/931 |

FOREIGN PATENT DOCUMENTS

0132990 2/1985 European Pat. Off. .

OTHER PUBLICATIONS

Chemical Abstracts, vol. 84, No. 9, Mar. 1, 1976, Abstract No. 58886u.

Chemical Abstracts, vol. 92, No. 18, May 5, 1980, Abstract No. 149476s.

*Primary Examiner*—Robert L. Stoll
*Assistant Examiner*—Greg M. Sweet
*Attorney, Agent, or Firm*—Nixon & Vanderhye

[57] ABSTRACT

A relatively fast process for producing HNS from trinitrotoluene (TNT) in high yield consists of oxidizing TNT with an oxidizing transition metal compound within a polar aprotic solvent having a weak base, such as an alkali metal carboxylate, dissolved therein. The amount of transition metal compound used is typically at least one mole per mole of TNT. An especially preferred transition metal compound for use in the present process is cupric chloride.

16 Claims, No Drawings

PRODUCTION OF HEXANITROSTILBENE (HNS)

This invention relates to the production of 2,2',4.4',6,6'-hexanitrostilbene (HNS) (also known as 1,2bis(2,4,6-trinitrophenyl)ethane) from 2,4,6,trinitrotoluene (TNT).

HNS is a thermally-stable explosive which is especially useful as a crystal-modifying additive in melt-cast TNT. The first unequivocal synthesis of HNS is disclosed in U.S. Pat. No. 3,505,413 (Shipp). This document describes a process for HNS production which is based on the reaction of TNT with sodium hypochlorite in tetrahydrofuran/methanol solution at 15° C. The crude HNS produced is washed in acetone to remove the bulk of coprecipitated impurities. The yield of HNS produced by this process is low, typically only about 30-35%, and the process also produces a large number of unwanted by-products, some of which are difficult to remove from the HNS product and from the recyclable tetrahydrofuran solvent. Later improvements to this process disclosed in the UK Patent Nos. 1513221 and 1570569 increased HNS yields to about 50%.

A further process for the production of HNS is disclosed in Hungarian Patent No. T/9639VE-719 (Kompolthy et al) which essentially consists of the oxidative coupling of TNT with free oxygen present in air. The reactions disclosed were carried out in the presence of methanolic potassium hydroxide solution, a polar aprotic solvent and optionally an oxidative catalyst consisting of anhydrous copper sulphate/pyridine or cobalt naphthenate, and were followed by the addition of a solution buffer and carboxylic acid to precipitate the production. Kompolthy et al also disclose that similar processes can be used for the production of the intermediate product DPE from TNT, and for the production of HNS from DPE (DPE=1,2dipicrylethane). Typically, they obtained crude yields of 30-55% HNS from TNT, indicating little if any improvement in yields over those disclosed in the above-mentioned UK Patents, though HNS yields of up to 90% from DPE were obtained using an anhydrous copper sulphate/pyridine catalyst. The yields were "crude" in the sense that the reported purification of the (precipitated) product did not generally extend beyond washing with water (to remove water-soluble impurities) followed by washing with methanol (to remove unreacted TNT); however this crude product was frequently found to be of sufficient purity (as measured by its melting point range) for use by the explosives industry. These yields were later generally confirmed by Golding and Hayes (Propellants and Explosives 4, 115-120 (1979)). However other workers have reportedly obtained yields of only 25-40% when repeating the DPE-to-HNS processes of Kompolthy et al.

In view of the poor yields and other difficulties outlined above which are associated with the processes of Shipp and Kompolthy et al for converting TNT directly to HNS, much recent research effort has been concentrated on the development of processes for converting the intermediate product 2,2',4,4',6,6'hexanitrobibenzyl (HNBB), also known as 1,2dipicrylethane (DPE), into HNS in high and reproducible yields. Such processes are described in the following U.S. Pat. Nos. 4,221,745 (reaction of HNBB with a copper salt and ammonium hydroxide in an aprotic solvent), 4,221,746 (reaction of HNBB with a halogen or organic halide in the presence of an aprotic solvent and a base), 4,243,614 (reaction of HNBB with a copper salt, especially copper sulphate, in an aprotic solvent with oxygen optionally added), 4,268,696 (reaction of HNBB with a quinone oxidant in an aprotic solvent, optionally in the presence of an organic amine base) and 4,270,012 (reaction of HNBB with oxygen in a aprotic solvent in the presence of a catalyst). Since HNBB can be produced in comparatively high yield by the process of Shipp (a yield of 79% is reported), using some of the above HNBB-to-HNS processes it it possible to obtain an overall TNT-to-HNS yield of some 70-75%. This is considerably better than the maximum yield of 55% mentioned above which could be obtained using the direct, one reaction-stage conversion of TNT to HNS disclosed by Shipp, Kompolthy et al, and others. However, these improved yields can only be achieved using a two-reaction stage TNT-to-HNS process via HNBB, with the drawback that additional processing time, equipment, and cost will normally be involved.

One process which partly overcomes the above disadvantages is disclosed in EP-0132990-A2 (Duffin et al). Here, a single stage process is described for converting TNT to HNS in moderately high yield by reacting TNT with oxygen in an aprotic solvent having a carboxylate base dissolved therein. Although this process possesses many advantages over the aforementioned processes for converting TNT to HNS, its main disadvantage is that the maximum crude yield disclosed using this process (65%, before washing with acetone to remove any DPE present) still falls short of that which could be achieved using one of the high yield HNBB-to-HNS processes mentioned above coupled with Shipp's TNT-to-HNBB process. Furthermore, the TNT-to-HNS process of Duffin et al is fairly slow, requiring a reaction time of 90 minutes at 25° C. to achieve the yields reported, and the reaction product is found to be difficult to isolate by filtration because of its generally sticky handling characteristics.

The present invention seeks to overcome, at least in part, the disadvantages of the above-mentioned processes by providing a novel process for preparing HNS which comprises oxidising a quantity of TNT to HNS in a reaction mixture comprising a solvent having a base dissolved therein, wherein at least 75 mol % of the quantity of TNT is oxidised with an oxidising transition metal compound contained within the reaction mixture. The transition metal is preferably selected from those having at least two oxidation states, the oxidation state of the metal in the compound being greater than the lower or lowest of these states. Most preferably, the oxidising compound is a compound of copper (II) or cobalt (III).

The oxidising compound is preferably a salt or complex of a transition metal, and is preferably provided in its anhydrous form. Any common oxidising salt or complex may be used provided it is at least partly (and is preferably fully) soluble in the solvent selected and does not react with any of the ingredients in the reaction mixture other than TNT and DPE. Advantageously, the oxidising compound is of a type which is readily soluble in water and so is easily separated from the HNS product by water washing, and which may be reoxidised in solution with oxygen after use.

Preferred salts include halides, especially chlorides, sulphates and nitrates, and preferred complexes are amino complexes. An especially preferred oxidising agent is cupric chloride. The mole ratio of oxidising compound to TNT in the reaction mixture at the commencement of the reaction is preferably from 0.75:1 to 10:1, more preferably from 1:1 to 5:1, most preferably from 1.25:1 to 4:1.

The reaction medium preferably contains the said transition metal oxidant as substantially its sole oxidising agent. Unexpectedly, the present inventors have found that the additional use of an oxygen-containing gas such as air, which is conventionally used to oxidise TNT to HNS, in the reaction medium actually has a detrimental effect on the process in that it generally reduces HNS yield and produces an HNS product which is sticky and difficult to filter.

The term "base" as used in this specification means a material which is capable of initiating the reaction to convert TNT (or DPE) to HNS, by promoting the removal of a proton from TNT (or DPE) under the reaction conditions. Thus the base may comprise any one of those bases which have conventionally been used in the art for converting TNT or DPE to HNS, though it is preferably selected from those normally regarded as weak bases in the solvents selected. It may comprise, for example, an organic amine having a pKa value of 4.5 to 6.5 such as one selected from those disclosed in U.S. Pat. No. 4,268,696 e.g. aniline, quinoline, N,N-dimethylaniline, pyridine, 2-picoline, and 4-picoline. Alternatively the base may be a weak base comprising a salt of an acid having an acid dissociation constant (Ka) value in water within the range $2\times10^{-4}$ to $10^{-6}$, preferably $2\times10^{-4}$ to $10^{-5}$. Examples of salts of acids which may be used as bases are to be found in U.S. Pat. No. 4,270,012 and include carboxylates, carbonates, bicarbonates, nitrites, and cyanides. Most preferably, however, the base comprises a salt of a carboxylic acid, especially a monocarboxylic acid. Such salts are disclosed in EP-0132990-A2. The cation of the salt is preferably an ammonium or alkali metal cation. The preferred molar ratio of base:TNT at the commencement of the reaction is from 2:1 to 8:1 and is most preferably from 3:1 to 6:1.

The present process is preferably performed at a temperature between 5° C. and 100° C., most preferably between 15° C. and 50° C. After completion of the reaction, which will usually take from 10 to 60 minutes, the reaction is conveniently quenched in water which may advantageously be acidified. Water washing of the resulting precipitate removes any water-soluble components in the reaction mixture, and washing with methanol and acetone removes any unreacted TNT and DPE byproduct respectively. High purity HNS may be prepared by subsequently recrystallising the water-and-solvent washed precipitate from a hot aprotic solvent such as dimethyl sulphoxide, but the present inventors have generally found that the only purification steps which are normally required to prepare HNS of an acceptable grade for most explosives uses are water washing followed by TNT removal (usually by methanol washing). This is because the product of the present invention is normally found to contain very little DPE or other water-insoluble byproducts.

The main advantage of the present invention is that it is capable of producing yields of explosive-quality HNS from TNT exceeding 75%, which is considerably higher than any of the yields reported in the above mentioned descriptions of known single-stage TNT-to-HNS processes. A further advantage of the present invention is that the reaction times required are comparatively short (typically 20-30 minutes) even when employing relatively mild reaction conditions (e.g. 25° C. reaction temperature and a very weak base such as sodium benzoate). These relatively short reaction times mean that for HNS production equipment of a given size, it will be generally possible to increase HNS throughput well above that which is achievable using the process of (for example) EP-0132990-A2. A yet further advantage of the present invention is that the product precipitate of the present process is generally found to be non-sticky and so more easily filtered than the product of the TNT-to-HNS process disclosed in EP-0132990-A2 which employs air oxidation.

The solvent employed is preferably a polar aprotic solvent and should be capable of dissolving the reactants and promoting the oxidative coupling on TNT to HNS in accordance with the present invention. In general, suitable solvents include those having average beta values within the range of about 0.65 to 1.1, preferably 0.70 to 1.0, on the beta-scale of solvent hydrogen bond acceptor (HBA) basicities according to page 382, Table III of the article by M. J. Kamlet and R. W. Taft in *J. Am Chem Soc.* 98, 377 (1976). The solvent is preferably selected from N,N-dimethylformamide (DMF), pyridine, N-methylpyrrolidone, hexamethylphosphoramide (HMPA), dioxan, N,N-dimethylacetamide, dimethylsulphoxide (DMSO), hexamethyl phosphoric triamide, dimethyl propylene urea (DMPU), dimethylethylene urea (DMEU), and mixtures thereof. The solvent is most preferably DMSO.

The present invention will now be described by way of Example only.

EXAMPLES 1-5

Direct Conversion of TNT to HNS using Cupric Chloride as Oxidant

Example 1

1 g ($4.40\times10^{-3}$ moles) TNT and 0.9 g ($6.69\times10^{-3}$ moles) of anhydrous cupric chloride were dissolved in 30 ml of DMSO at 25° C. and placed in a reaction vessel equipped with a stirrer. 2.1 g ($1.46\times10^{-2}$ moles) of sodium benzoate was then added to the vessel with stirring. The reaction mixture was subsequently maintained at 25° C. for 30 minutes, with continuous stirring. At the end of this period the mixture was poured into excess water. After standing for about 10 minutes to allow formation of the precipitate, the non-sticky solid formed was filtered off and washed firstly with distilled water, and then with methanol. The residual insoluble material remaining after these washes was found to be HNS. This was dried and weighed. Yield: 0.8 g ($1.78\times10^{-3}$ moles) 80%, melting point 308°-316° C. The melting point of this HNS product indicated that its purity would be acceptable for most explosives applications.

Example 2

The reaction and recovery procedure of Example 1 was repeated but utilising only 0.6 g of cupric chloride which yielded only 0.5 g ($1.11\times10^{-3}$ moles) on HNS (i.e. 50% yield).

Example 3

The reaction and recovery procedure of Example 2 was repeated, but with only 20 minutes reaction time. This procedure yielded 0.76 g ($1.69\times10^{-3}$ moles) of HNS (i.e. 76% yield).

Example 4

The reaction and recovery procedure of Example 1 was repeated but utilising sodium formate ($1.46 \times 10^{-2}$ moles) instead of sodium benzoate, with a 20 minute reaction time yielded 0.7 g. ($1.56 \times 10^{-3}$ moles) of HNS (i.e. 70% yield).

Example 5

The reaction and recovery procedure of Example 1 was repeated, but utilising 30 ml of a 1:1 volume mixture of DMSO and Dioxan instead of pure DMSO. This procedure yielded 0.7 g ($1.56 \times 10^{-3}$ moles) of HNS (i.e. 70% yield).

The following Examples all relate to the preparation of high purity HNS, in which the crude HNS product prepared in accordance with general procedure specified in Example 1 were further purified first by washing in acetone (to remove any residual DPE, although the amount present did not usually exceed 4% by weight of the original quantity of TNT), and then by recrystallisation from hot DMSO. Additional losses through further purification steps (including losses of HNS in the DMSO solvent) were found typically to be of the order of 15% by weight. In some instances the water used to quench the reaction was acidified with 1% (w/v) concentrated hydrochloric acid.

EXAMPLES 6 TO 15

Direct Conversion of TNT to HNS using Cupric Chloride as Oxidant

Volume of solvent = 30 ml
Conc. of TNT in solvent = 0.1225 mol $1^{-1}$ (1.0 g)
Conc. of base (potassium formate) = see Table 1 below
Reaction Time = 20 minutes

TABLE 1

| Example | conc of base mol $1^{-1}$ | conversion to HNS (%) | conversion to DPE (%) | other materials (%) |
|---|---|---|---|---|
| conc of CuCl$_2$ = 0.122 mol $1^{-1}$ | | | | |
| 6. | 0.238 | 22 | 6 | 70 |
| 7. | 0.357 | 40 | 4 | 54 |
| 8. | 0.476 | 48 | 4 | 44 |
| 9. | 0.595 | 42 | 3 | 51 |
| conc of CuCl$_2$ = 0.247 mol $1^{-1}$ | | | | |
| 10. | 0.238 | 29 | 4 | 66 |
| 11. | 0.357 | 54 | 4 | 40 |
| 12. | 0.476 | 61 | 2 | 36 |
| 13. | 0.595 | 56 | — | 40 |
| conc of CuCl$_2$ = 0.371 mol $1^{-1}$ | | | | |
| 14. | 0.476 | 40 | — | 56 |
| 15. | 0.595 | 51 | — | 46 |

EXAMPLES 16 TO 24

Direct Conversion of TNT to HNS using Cupric Chloride as Oxidant

Volume of solvent (DMSO) = 30 ml
Conc. of TNT in solvent = 0.1225 mol $1^{-1}$
Conc. of base (sodium benzoate) = see Table 2 below
Reaction Time = 20 Minutes

TABLE 2

| Example | conc of base mol $1^{-1}$ | conversion to HNS (%) | conversion to DPE (%) | other materials (%) |
|---|---|---|---|---|
| conc of CuCl$_2$ = 0.124 mol $1^{-1}$ | | | | |
| 16. | 0.360 | 43 | 3 | 51 |
| 17. | 0.471 | 49 | — | 48 |
| 18. | 0.588 | 46 | — | 49 |
| conc of CuCl$_2$ = 0.249 mol $1^{-1}$ | | | | |
| 19. | 0.241 | 28 | 6 | 62 |
| 20. | 0.356 | 56 | 1 | 43 |
| 21. | 0.468 | 66 | — | 31 |
| 22. | 0.592 | 64 | — | 34 |
| conc of CuCl$_2$ = 0.380 mol $1^{-1}$ | | | | |
| 23. | 0.479 | 44 | — | 56 |
| 24. | 0.598 | 54 | — | 43 |

EXAMPLES 25 TO 28

Direct Conversion of TNT to HNS using Cupric Chloride as Oxidant

Volume of solvent = 30 ml
Conc. of TNT in solvent = 0.123 mol $1^{-1}$
Reaction Time = 20 minutes
Conc. of base (sodium acetate) = see Table 3 below
Conc. of CuCl$_2$ = 0.378 mol$^{-1}$

TABLE 3

| Example | conc of base mol $1^{-1}$ | conversion to HNS (%) | conversion to DPE (%) | other materials (%) |
|---|---|---|---|---|
| 25. | 0.254 | 26 | 5 | 64 |
| 26. | 0.361 | 48 | 1 | 50 |
| 27. | 0.470 | 54 | — | 42 |
| 28. | 0.590 | 51 | — | 46 |

EXAMPLES 29 TO 36

Direct Conversion of TNT to HNS using Anhydrous Cupric Sulphate as Oxidant

Volume of solvent (DMSO) = 30 ml
Conc. of TNT in solvent = 0.123 mol $1^{-1}$
Conc of base (sodium benzoate) = see Table 4 below
Reaction Time = 20 minutes

TABLE 4

| Example | conc of base mol $1^{-1}$ | conversion to HNS (%) | conversion to DPE (%) | other materials (%) |
|---|---|---|---|---|
| Conc. of CuSO$_4$ = 0.13 mol $1^{-1}$ | | | | |
| 29. | 0.238 | 20 | 6 | 71 |
| 30. | 0.357 | 41 | 8 | 48 |
| 31. | 0.476 | 46 | 4 | 43 |
| 32. | 0.60 | 40 | 3 | 52 |
| Conc. of CuSO$_4$ = 0.25 mol $1^{-1}$ | | | | |
| 33. | 0.238 | 24 | 5 | 68 |
| 34. | 0.357 | 51 | 4 | 44 |
| 35. | 0.476 | 62 | — | 36 |
| 36. | 0.60 | 54 | — | 45 |

EXAMPLES 37 TO 44

Direct Conversion of TNT to HNS using Cobalt Hexamine Trichloride as Oxidant

Volume of solvent (DMSO) = 30 ml
Conc. of TNT in solvent = 0.073 mol $1^{-1}$
Conc. of base (sodium benzoate) = see Table 5 below
Reaction Time = 40 minutes

TABLE 5

| Example | conc of base mol $l^{-1}$ | conversion to HNS (%) | conversion to DPE (%) | other materials (%) |
|---|---|---|---|---|
| Conc of Co(NH$_3$)$_6$CL$_3$ = 1.4 × 10$^{-1}$ mol l$^{-1}$ | | | | |
| 37. | 14.54 × 10$^{-2}$ | 14 | 18 | 64 |
| 38. | 21.65 × 10$^{-2}$ | 34 | 12 | 50 |
| 39. | 28.15 × 10$^{-2}$ | 48 | 8 | 41 |
| 40. | 36.41 × 10$^{-2}$ | 42 | 6 | 51 |
| Conc of Co(NH$_3$)$_6$Cl$_3$ = 2.9 × 10$^{-1}$ mol l$^{-1}$ | | | | |
| 41. | 14.54 × 10$^{-2}$ | 28 | 20 | 46 |
| 42. | 21.65 × 10$^{-2}$ | 41 | 24 | 31 |
| 43. | 28.15 × 10$^{-2}$ | 59 | 11 | 24 |
| 44. | 36.41 × 10$^{-2}$ | 58 | — | 40 |

EXAMPLES 45 TO 48

Direct Conversion of TNT to HNS using Cobalt Hexamine Trichloride as Oxidant

Volume of solvent (DMSO) = 30 ml
Conc. of TNT in solvent = 0.0735 mol l$^{-1}$
Conc. of base (potassium formate) = see Table 6 below
Conc. of [Co(NH$_3$)$_6$]Cl$_3$ = 0.284 mol l$^{-1}$
Reaction Time = 40 minutes

TABLE 6

| Example | conc of base mol $l^{-1}$ | conversion to HNS (%) | conversion to DPE (%) | other materials (%) |
|---|---|---|---|---|
| 45. | 14.54 × 10$^{-2}$ | 24 | 14 | 60 |
| 46. | 21.65 × 10$^{-2}$ | 39 | 12 | 41 |
| 47. | 28.15 × 10$^{-2}$ | 61 | 1 | 34 |
| 48. | 36.41 × 10$^{-2}$ | 60 | — | 37 |

We claim:

1. A process for preparing 2,2',4,4',6,6'-hexanitrostilbene which comprises oxidizing 2,4,6-trinitrotoluene directly to 2,2',4,4',6,6'-hexanitrostilbene in the same reaction mixture throughout, the reaction mixture comprising a solvent having a base dissolved therein and containing an oxidizing transition metal compound in an amount of from 0.75 to 10 moles of said oxidizing compound per mole of 2,4,6-trinitrotoluene.

2. A process according to claim 1, wherein the transition metal has at least two oxidation states and the oxidation state of the transition metal in the oxidising compound is greater than the lower or lowest of these at least two oxidation states.

3. A process according to claim 2 wherein the oxidising compound comprises a salt or a complex of a transition metal.

4. A process according to claim 3 wherein the oxidising compound comprises a halide, a sulphate or a nitrate.

5. A process according to claim 2 wherein the oxidising compound is a compound of copper (II) or cobalt (III).

6. A process according to claim 1, wherein the amount of oxidizing transition metal compound employed in the reaction mixture is from 1 to 5 moles per mole of 2,4,6-trinitrotoluene.

7. A process according to claim 1, wherein the base is an organic amine having a pKa value of 4.5 to 6.5.

8. A process according to claim 1, wherein the base is a weak base comprising a salt of an acid having a Ka value in water of between 2×10$^{-4}$ and 10$^{-6}$.

9. A process according to claim 8 wherein the weak base is a salt of an acid having a Ka value in water of between 2×10$^{-4}$ and 10$^{-5}$.

10. A process according to claim 1, wherein the base is a salt of a carboxylic acid.

11. A process according to claim 1, wherein the molar ratio of base to 2,4,6-trinitrotoluene at the commencement of the reaction is from 2:1 to 8:1.

12. A process according to claim 1 wherein the solvent is a polar aprotic solvent or a mixture of polar aprotic solvents.

13. A process according to claim 12 wherein the solvent has an average beta value, on the beta-scale of solvent hydrogen bond acceptor (HBA) basicities, within the range 0.65 to 1.1.

14. A process according to claim 1, wherein the solvent is selected from the group consisting of N,N-dimethylformamide, pyridine, N-methylpyrrolidone, hexamethylphosphoramide, dioxan, N,N-dimethylacetamide, dimethylsulphoxide, hexamethyl phosphoric triamide, dimethyl propylene urea, and mixtures thereof.

15. A process according to claim 1, wherein the reaction is performed at a temperature between 5° C. and 100° C.

16. A process according to claim 1, wherein the reaction time is between 10 and 60 minutes.

* * * * *